US005765722A

United States Patent [19]
Beebe et al.

[11] Patent Number: 5,765,722
[45] Date of Patent: *Jun. 16, 1998

[54] ELECTRONICALLY CONTROLLED, POSITIVE-DISPLACEMENT FLUID DISPENSER

[75] Inventors: W. Scott Beebe, Ashland; Michael J. Leuschner, Framingham; Joseph S. Barresi, Holliston, all of Mass.

[73] Assignee: Fishman Corporation, Hopkinton, Mass.

[*] Notice: The term of this patent shall not extend beyond the expiration date of Pat. No. 5,630,527.

[21] Appl. No.: 670,458

[22] Filed: Jun. 26, 1996

Related U.S. Application Data

[63] Continuation-in-part of Ser. No. 304,267, Sep. 12, 1994, Pat. No. 5,630,527.
[51] Int. Cl.[6] .................................................. B67B 7/00
[52] U.S. Cl. ........................... 222/1; 222/63; 222/327; 222/390
[58] Field of Search ...................... 222/1, 63, 137, 222/325, 326, 327, 333, 390; 604/155, 224

[56] References Cited

U.S. PATENT DOCUMENTS

| | | | |
|---|---|---|---|
| 4,335,834 | 6/1982 | Zepkin | 222/63 |
| 4,950,134 | 8/1990 | Bailey et al. | 417/383 |
| 5,188,259 | 2/1993 | Petit | 222/333 X |
| 5,348,585 | 9/1994 | Weston | 222/63 X |
| 5,630,527 | 5/1997 | Beebe et al. | 222/1 |

*Primary Examiner*—Gregory L. Huson
*Attorney, Agent, or Firm*—Timothy J. Shea, II, Esq.

[57] ABSTRACT

A fluid dispenser system, and method of use thereof primarily in industrial applications requiring the dispensing of fluids with varying viscosities, such as water, epoxies, silicones, adhesives, single component, two component, filled, premixed, frozen, etc., allowing for very precise control of the volume of fluid extruded. The system comprises an ergonomic, handheld applicator accommodating a conventional medical syringe, wherein the ergonomic, handheld applicator is attached by a power cord to an electronic control unit. The applicator is provided with a linear actuator that drives a piston or screw a specific distance in response to an electronic signal generated by the control unit. Displacement of the piston or screw creates a positive pressure on a fluid contained in the syringe, thereby causing fluid extrusion from the syringe.

23 Claims, 5 Drawing Sheets

ELECTRONICALLY CONTROLLED, POSITIVE-DISPLACEMENT FLUID DISPENSER

This application is a continuation-in-part of U.S. application Ser. No. 08/304,267 filed on 12 Sep. 1994, now U.S. Pat. No. 5,630,527.

FIELD OF THE INVENTION

The present invention relates to a fluid dispenser system and method of use thereof, primarily in industrial applications requiring the dispensing of fluids with varying viscosities, such as water, epoxies, silicones, adhesives, single component, two component, filled, premixed, frozen, etc., although other applications, such as use in dentistry and the food service industry, are certainly anticipated.

BACKGROUND OF THE INVENTION

Dispensing consistent, controllable, measured amounts of fluids with varying viscosities at an assembly plant workstation is a long-standing problem facing manufacturers concerned with precision product assembly and business efficiency. As can be imagined, it is imperative that the optimum amount of fluid be dispensed if a quality good is to be produced. If too little fluid is dispensed, the product might be unsafe to use as designed. If too much fluid is dispensed, the product might be unsightly, messy, or unsafe; further, wasted fluid results in significant cost inefficiencies.

One solution to this problem is to provide a handheld applicator having a reservoir of fluid and attached to a source of the driving force needed to extrude the fluid. Use of a medical syringe as a reservoir and of a pressure-driven piston to provide the driving force on the fluid to be extruded are known in the art. The extant devices most similar to the present invention are the syringe pump and the pneumatic pressure-driven fluid dispenser. However, neither of these devices reads on the presently claimed invention.

A syringe pump is a medical device that continuously introduces a fluid into an intravenous tube. These devices usually employ a gravity-fed tube attached to a reservoir (usually an intravenous bag or bottle) and a motor-driven pump that regulates the flow of fluid via a cam that alternately compresses and releases the tube. This technology is not applicable to the high precision manufacturing requirements of industry.

More pertinent to the industrial context is the pneumatic pressure-driven fluid dispenser, which has a medical syringe used to store and apply the fluid to be dispensed attached to a control unit, where the control unit in turn is attached to a compressed air supply (usually "shop air"). Fluid is dispensed when a controlled burst of pneumatic pressure depresses the syringe plunger a specific distance. The major disadvantage of this technology is that, as fluid is dispensed, an increasing void volume is created behind the syringe plunger. Thus, since the same volume of compressed air is introduced to the syringe behind the plunger regardless of the void volume of the syringe, there is great variability during the course of emptying one syringe in the amount of fluid actually dispensed in each application.

It has been recognized that mechanical control of a syringe plunger would increase the accuracy and consistency of fluid dispensing. U.S. Pat. No. 4,598,840 to Burg shows apparatus capable of dispensing precise volumes of fluid, e.g., diluents such as chemical reagents, that have either been aspirated from independent containers or contained in removable, valveless fluid cartridges that have been inserted into the dispenser. The Burg device comprises a dispenser unit that accommodates a fluid cartridge. A tubular passageway is in fluid communication with the fluid cartridge at one end and, after passing through a handheld body element/tube guide element known as a hand probe, terminates in an open end. Fluid is either dispensed from or aspirated into the tubular passageway via the open end. The fluid is forced into the tubular passageway by a sealed pumping mechanism contained in the fluid cartridge and controlled by linear actuator motors contained in the dispenser unit. It is important to note that there is no contact between the linear actuators and a mountable, commercially available syringe. The Burg device uses a closed or sealed passageway for withdrawing and dispensing fluids. The closed passageway is critical to ensure that proper amounts of fluid that have not mixed with air are dispensed or aspirated. The device is intended primarily for handling extremely small and fixed amounts of diluent having very low viscosities, such as in a scientific laboratory.

One drawback of the Burg system is that the unit has to have separate diluent cartridges attached, thus not allowing the unit to be rack mounted and placed in a production assembly line setting. A second drawback is that the device is designed for use with fluids having low viscosity, and not for a wide range of viscosities.

U.S. Pat. No. 4,634,431 to Whitney et al. shows a fixed dispenser having a complicated gearing mechanism controlled by a stepper motor. Further, Whitney et al. contemplates a syringe injector having a plunger disposed within the syringe barrel and a driver positioned behind the plunger. The rotational force generated by the stepper motor turns the driver and is, in turn, translated into longitudinal force against the plunger to dispense fluid from the syringe.

One drawback of the Whitney et al. dispenser is that it uses rotational movement, rather than axial movement, of the driver to dispense fluid. Another drawback, for industrial applications, is that the Whitney et al. dispenser is designed for use in the medical field for injecting low viscosity fluids into a patient and is not suitable for dispensing fluids having a wide range of viscosities. A third drawback is that the Whitney et al. dispenser cannot be used with conventional production assembly line equipment because of its lack of rigidity.

U.S. Pat. No. 5,219,099 to Spence et al. shows a syringe pump that uses a stepper motor to rotate a lead screw to drive a syringe plunger. The lead screw is coupled to the stepper motor by a flexible coupling, the combination together with the syringe being rigidly affixed to a reference member. One drawback of this dispenser is its use of a flexible coupling between the stepper motor and the lead screw. Another drawback is that the system requires that its parts are rigidly affixed to a reference member.

U.S. Pat. No. 5,348,585 to Weston shows a liquid dispensing apparatus that is mounted on an X-Y table. The Weston apparatus also uses a stepper motor to control the amount of fluid to be dispensed. This system does not allow for a free-standing, ergonomically designed applicator unit to be used by the operator. A second drawback is the complexity of the mechanically interconnecting means for securing a syringe and the stepper motor.

U.S. Pat. No. 4,848,606 to Taguchi et al. shows an apparatus for dispensing a predetermined volume of paste-like fluid that has a motor attached to one end of a threaded screw rod and a nozzle holder functionally connected to the screw rod. To control the Z-axis position of the nozzle, the motor is operated, thereby rotating the screw rod and causing the nozzle holder to travel up and down the rod threads. The dispensing is accomplished by a second motor and screw rod combination, this time having a piston-driving device coupled to a piston that is disposed within the nozzle. Operation of the second motor rotates the second screw rod, causing axial movement of the piston and subsequent fluid dispensing from the nozzle.

One drawback of the Taguchi et al. device is that it uses an indirect mechanical coupling between the rotating motor and the piston or plunger of a dispenser. Another drawback is that it cannot be rack-mounted and put into a production assembly line system. A third drawback is that it is dependent on being rigidly mounted to a reference member and cannot be adapted for handheld dispensing.

However, the fundamental drawback to the Weston Spence et al., and Taguchi et al. devices is that they dispense fluid from a syringe by moving the syringe, not the rod that drives the syringe plunger (i.e., by moving the "nut," not the "bolt"). Because these devices employ stepper motors, rotation of the rods attached thereto by definition results in axial movement of the means holding the syringe and, thus, the syringe itself, not of the rod and a plunger attached thereto. This is because stepper motors must be attached to the end of the rod that they drive, they do not allow the rod to pass through the axis of the motor such that the rod can move axially relative to the motor. This construction prevents the use of the Weston Spence et al., and Taguchi et al. devices in a handheld context. Indeed, Taguchi et al. compound this drawback by requiring two stepper motors and two drive rods, one to control the axial position of the nozzle and one to dispense fluid.

Another major drawback of all these conventional dispensers is that the "dosage" of fluid to be extruded cannot be controlled as precisely as desired. In addition, none of the above mentioned references use the latest technologies found in linear actuators to impart axial motion to a syringe plunger. Most of the references use translated rotational motion to create relative linear movement of a plunger, whether by driving a plunger along the threaded member or using the threaded member to drive other mechanical plunger-driving means.

In contrast, use of a linear actuator instead of a stepper motor would allow the rod itself to be driven axially through the actuator (i.e., moving the "bolt," not the "nut"). Thus, rotation of the linear actuator would result in the rotation and accompanying axial displacement of the rod relative to the linear actuator, thereby achieving direct control of a syringe plunger without complex mechanical means. Furthermore, this construction would allow for an ergonomic, handheld dispenser applicator design.

In addition to enabling precise volumetric control and ease of use, the ideal fluid dispenser should be an unobtrusive component in an assembly line workstation. It should conveniently be in reach of the worker, yet not impede the assembly process. Moreover, because rigidity of the syringe is essential, the syringe should be securely held by the dispenser applicator such that the syringe does not "cant" relative to the dispenser axis. However, because it is envisioned that bent needles will be used to apply fluid to the workpiece, the syringe should be allowed to rotate about the dispenser axis, to facilitate handheld operation.

Another feature that is found lacking in prior art devices is attachment of the syringe plunger to the drive rod. In addition to increasing the accuracy of fluid dispensing, connecting the plunger to the drive rod enables the operator to "back off" the plunger to enhance extrusion of highly viscous fluids and to permit the operator to refill the syringe by retracting the plunger from the barrel, thereby creating a vacuum that will draw fluids into the syringe barrel.

Further, because of the significant physical and economic costs associated with repetitive motion syndrome (a.k.a. "carpal tunnel syndrome"), it is desirable that the dispenser applicator have an ergonomic design to minimize the incidence in assembly workers of injuries due to this syndrome. Finally, because handheld operation is desirable, the dispenser applicator should weigh as little as possible, yet still retain high degrees of durability and rigidity.

The present invention provides an elegant solution to all of these problems.

SUMMARY OF THE INVENTION

The present invention is a fluid dispenser system, and method of use thereof primarily in industrial applications requiring the dispensing of fluids with varying viscosities, such as water, epoxies, silicones, adhesives, single component, two component, filled, premixed, frozen, etc., allowing for very precise control of the volume of fluid extruded.

The fluid dispenser allows a conventional syringe to be disposed within an adapter unit that is attached to an ergonomically handheld dispenser apparatus that may move freely in any direction. This ergonomically handheld apparatus is furthermore controlled by a microprocessor-based control unit that can be programmed to dispense precise volumes of fluids based on syringe size, including length, inside diameter, dispense volume, dispense rate, backoff, method of dispensing, and control of automated or manual dispense actions, and fluid viscosity.

The ergonomic, handheld or mountable applicator has an infinite degree of motion freedom. The control unit can be rack mounted for ease of use in a production assembly line and the ergonomic, handheld applicator can be mounted to existing commercially available X-Y-Z axis tables, wherein the volume of fluid dispensed can be programmed by the control unit or regulated by an external source to maintain the desired volumes at the desired rates. The control unit and the ergonomic, handheld applicator are not affixed to a reference member and can be freely portable within a production facility, or work setting.

The system comprises an ergonomic, handheld applicator capable of accommodating a conventional syringe and piston assembly, wherein the ergonomic, handheld applicator is attached by a control tether to an electronic control unit. The applicator is provided with a linear actuator that displaces a drive rod a specific distance in response to an electronic drive signal generated by the control unit. The electronic drive signal is generated by the control unit in response to receipt of an actuator signal generated by either the operator, as by a fingerswitch attached to the handheld applicator or a footpedal, or a pre-programmed input, such as a microprocessor. Displacement of the drive rod creates a positive pressure on a fluid contained in the syringe, thereby causing fluid extrusion from the syringe. As can be expected, because the drive rod is displaced a precise distance, this system allows for very precise control of the volume of fluid extruded.

Prior to this invention, only approximate volumes of fluid were able reliably to be extruded from a handheld applicator. In addition to potentially dispensing either too much or too little fluid, such dispensers were difficult to control and very inefficient delivery systems. A further problem is the relatively high incidence of repetitive motion syndrome among those using prior known devices.

The significance of the present invention is that it enables a precise and optimum amount of fluid to be dispensed in a manner that results in greater cost efficiency and reduces the incidence of worker injury due to repetitive motion syndrome.

Accordingly, an object of the present invention is to provide a means for dispensing a precise and optimum amount of fluid. A further object of the present invention is to provide a fluid dispensing means having sufficient rigidity, durability, and light weight to meet production line requirements. Another object of the present invention is to provide such a dispensing means that does not pose a significant risk of injury due to repetitive motion syndrome. Yet another object of the present invention is to provide a fluid dispensing means that drives a rod having a plunger attached thereto axially relative to a securely, yet rotatably, held syringe. Further objects and advantages of the invention will become apparent from the description of the drawings and the invention, which follow.

DESCRIPTION OF THE PREFERRED EMBODIMENTS

Figure 1:
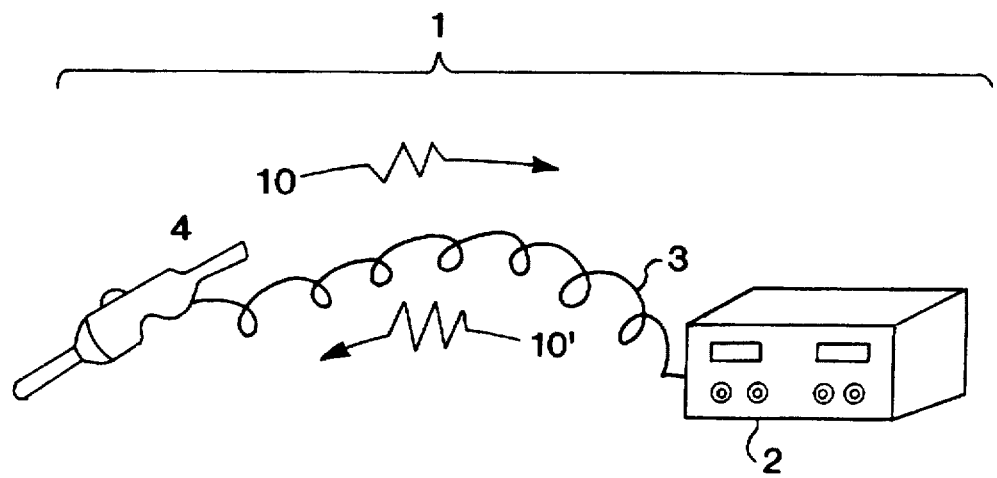
FIG. 1 is a schematic diagram of one embodiment of the electronically controlled, positive-displacement fluid dispenser system presently claimed.
Figure 2:
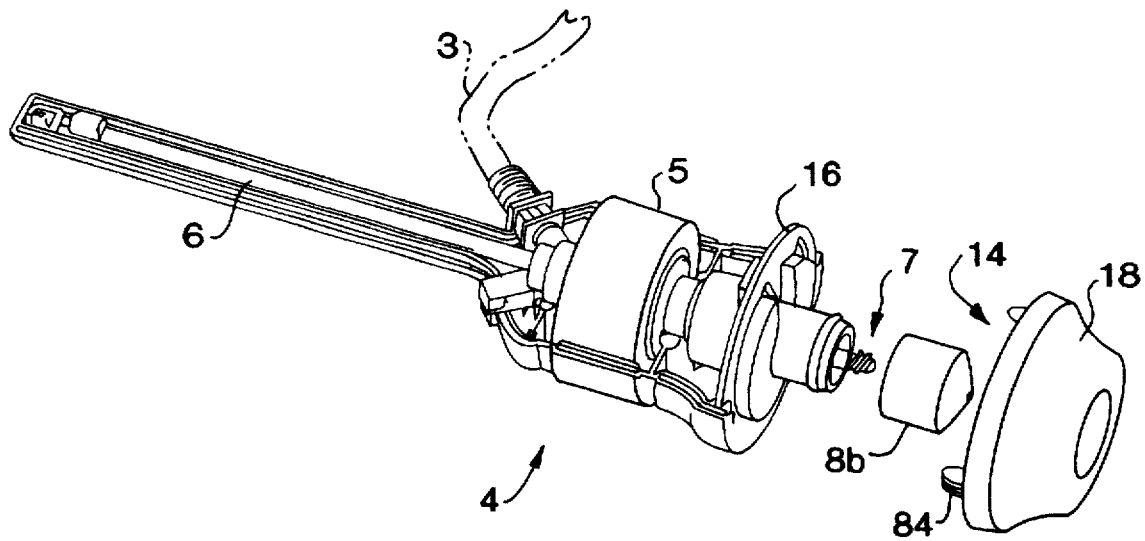
FIG. 2 shows a side view of one configuration of the ergonomically designed handheld applicator of the present invention.
Figure 3:
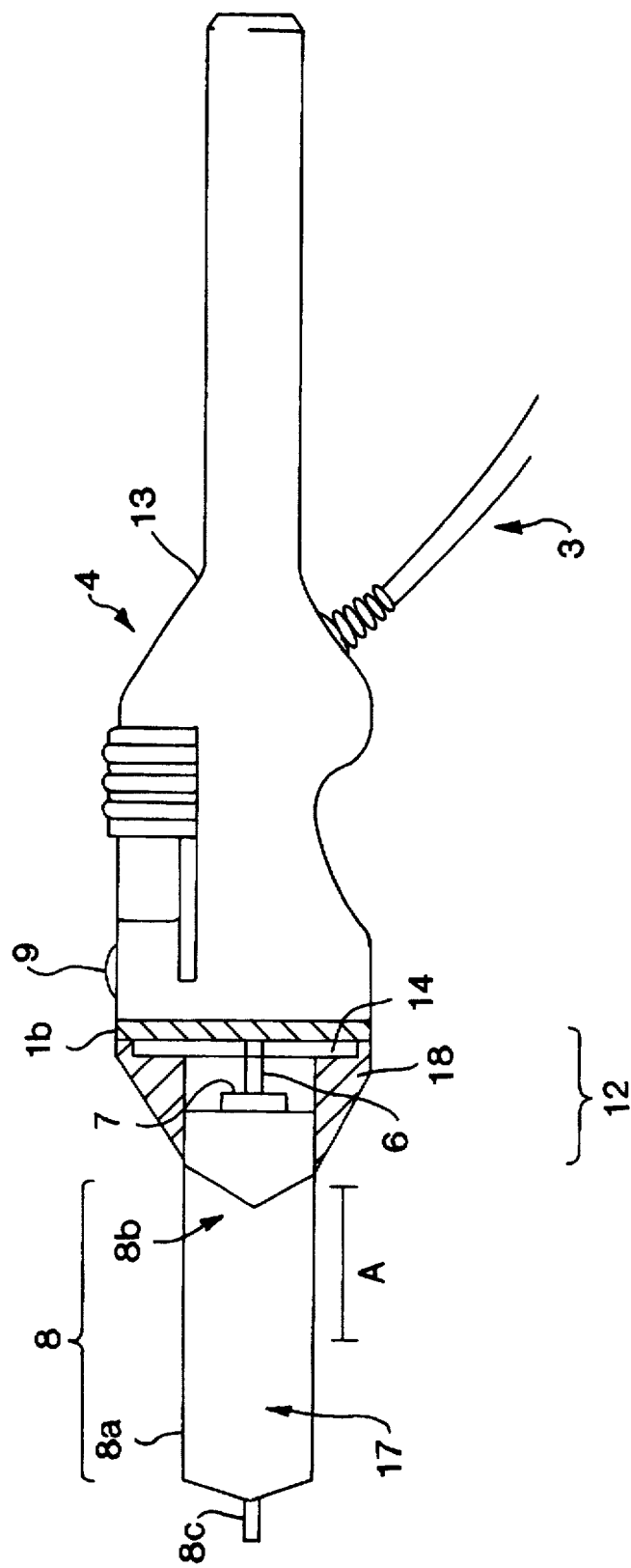
FIG. 3 shows the ergonomically designed handheld applicator of FIG. 2 in combination with a conventional syringe and piston assembly.

An electronically controlled, positive-displacement fluid dispenser system is provided. The dispenser is primarily constructed of elements made from durable, lightweight materials. As shown in FIGS. 1, 2, and 3, the dispenser system 1 comprises a control unit 2 attached by a control tether 3 to an ergonomically designed handheld applicator 4. The control tether may be advantageously positioned on the handheld applicator so as to minimize both interference with the assembly operation and also stress on the operator's wrist and arm.

Figure 10:
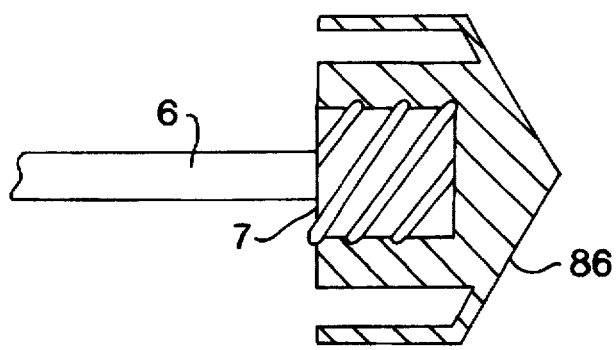
FIG. 10 shows one embodiment, of the drive rod/plunger assembly.

Handheld applicator 4 is provided with a linear actuator 5 having drive rod 6 axially and engagably disposed therethrough. Drive rod 6 is provided with engagable terminus 7. Drive rod 6 inserts into a conventional syringe 8a and piston 8b assembly 8 for storage and application of the fluid 17 to be dispensed. Syringe 8a has a nozzle 8c adapted to accommodate conventional applicator needles. As shown in FIG. 10, engagable terminus 7 is designed to engage with piston 8b, so as to allow precise axial movement of piston 8b during both insertion of piston 8b into and withdrawal from syringe 8a.

Figure 8A:
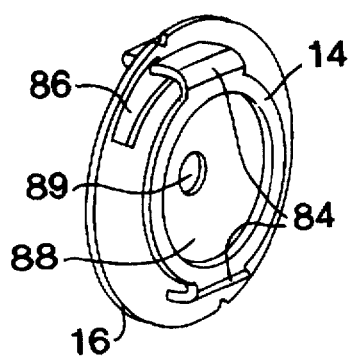
FIG. 8A shows a perspective view of one embodiment of the syringe adapter unit.
Figure 8B:
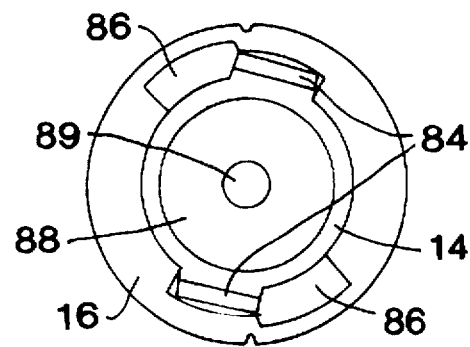
FIG. 8B shows a plan view of the embodiment of FIG. 8A.
Figure 9A:
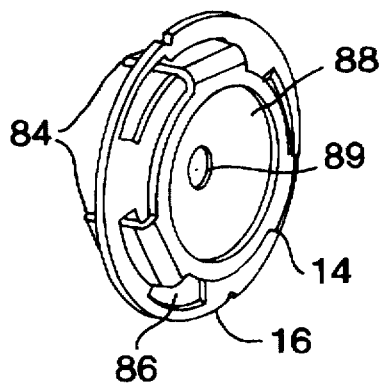
FIG. 9A shows a perspective view of a second embodiment of the syringe adapter unit.
Figure 9B:
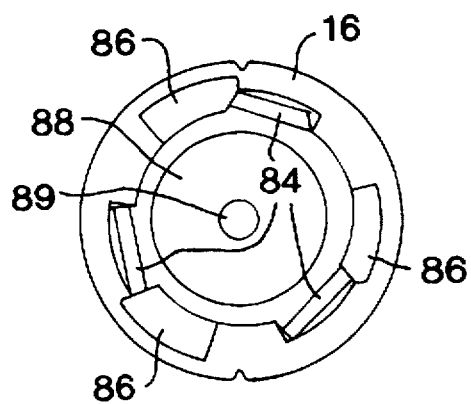
FIG. 9B shows a plan view of the embodiment of FIG. 9A.

As shown in FIGS. 8–9, syringe 8 is securely combined with dispenser 4 by means of adapter unit 12, which comprises retaining ring 14 and adapter plate 16. Retaining ring 14 has a plurality of locking tabs 84 disposed about the periphery of retaining ring 14 such that locking tabs 84 are disposed at a relatively normal angle from retaining ring 14. Retaining ring 14 further defines an axial void 88 capable of accommodating a conventional medical syringe barrel. Adapter plate 16 is a planar member that defines a corresponding plurality of peripheral voids 86 capable of accommodating the plurality of locking tabs 84 such that rotation of retaining ring 14 relative to adapter plate 16 results in locking tabs 84 being locked into peripheral voids 86. Adapter plate 16 further defines an axial void 89 suitable for accommodating drive rod 6. It is intended that adapter unit 12 be disposed within ergonomically designed cowling 18, although other constructions are possible, such as forming one face of retaining ring 14 into an ergonomically suitable shape.

Control unit 2 may allow the dispenser operator to select either pre-programmed fluid volumes and flowrates or a variable volume and flowrate, as required. When the operator depresses finger switch 9, which is an actuator signal generator, an actuator signal 10 is sent via control tether 3 to the control unit 2, which processes the actuator signal 10 in accordance with the pre-selected fluid volume(s) and flowrate(s) and generates an electronic drive signal 10' of fixed duration, which is transmitted via control tether 3 to linear actuator 5. Linear actuator 5 then displaces drive rod 6 a specific axial distance A to extrude the precise volume of fluid 17 desired. It is important to note that, in this mode, the duration of electronic drive signal 10' is not affected by the length of time that the operator depresses finger switch 9.

In this embodiment, the duration of drive signal 10' is calculated to cause drive rod 6 to be displaced a specified distance, thereby ensuring that the desired, metered volume of fluid is extruded. However, if the operator elects manual control, the duration of drive signal 10', and, thus, fluid extrusion, is controlled by the operator via finger switch 9. Fluid will then be extruded at the selected flowrate for as long as finger switch 9 is depressed. Thus, in either mode of operation, the volume of fluid dispensed is controlled by regulating the duration of drive signal 10'.

Figure 4:
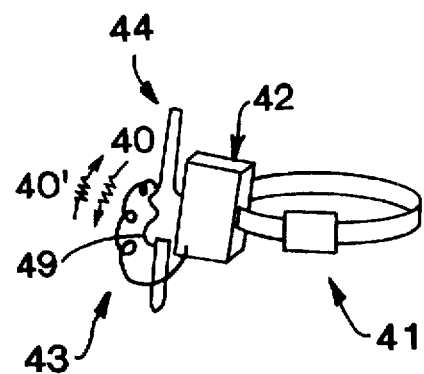
FIG. 4 shows an embodiment of the invention wherein the control unit has an internal power supply, thereby allowing for portable operation.

A further embodiment is shown in FIG. 4, wherein control unit 42 has an internal power supply, thereby allowing for portable operation. When the operator depresses finger switch 49, an actuator signal 40 is sent via control tether 43 to the control unit 42, which processes the actuator signal 40 in accordance with the pre-selected fluid volume(s) and flowrate(s) and generates an electronic drive signal 40' of fixed or variable duration, depending upon whether automatic or manual control has been selected, which drive signal is transmitted via control tether 43 to applicator 44. In this embodiment, the entire dispenser system could be worn as a belt pack 41.

Figure 5:
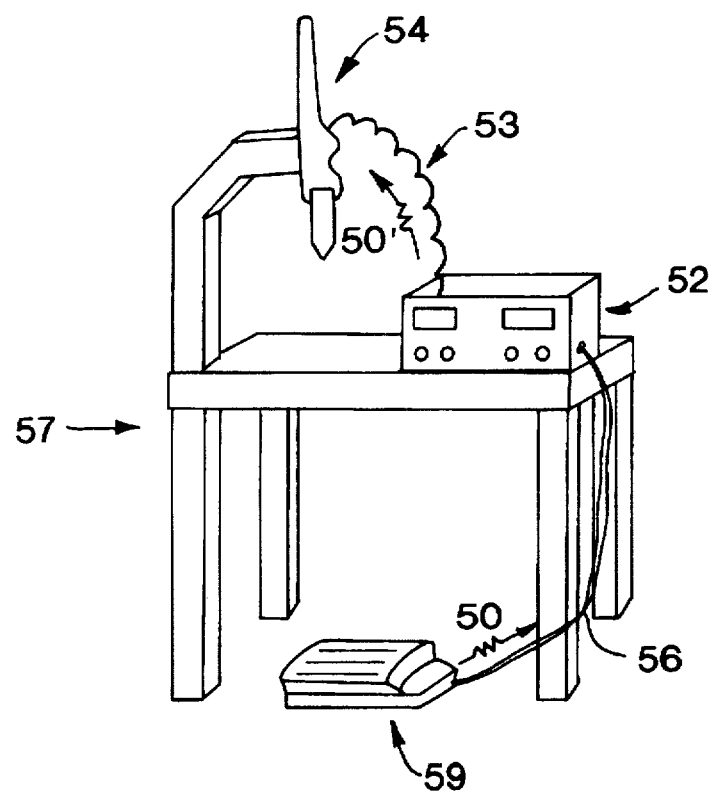
FIG. 5 shows the fluid dispenser system of the present invention stand-mounted and controlled via a footpedal.

An additional embodiment is shown in FIG. 5, wherein the applicator 54 is mounted to a stand 57 and controlled via a footpedal 59. In this embodiment, footpedal 59 is connected to control unit 52 by input tether 56. Actuator signal 50 is generated when footpedal 59 is depressed by the operator. Control unit 52 receives actuator signal 50 via input tether 56 and, in turn, generates drive signal 50' based on whether automatic or manual control been selected by the operator. Drive signal 50' is transmitted to applicator 54 via output tether 53. In a related embodiment, footpedal 59 is replaced with an electric eye, such that actuator signal 50 is generated when the electric eye beam is interrupted.

Figure 6:
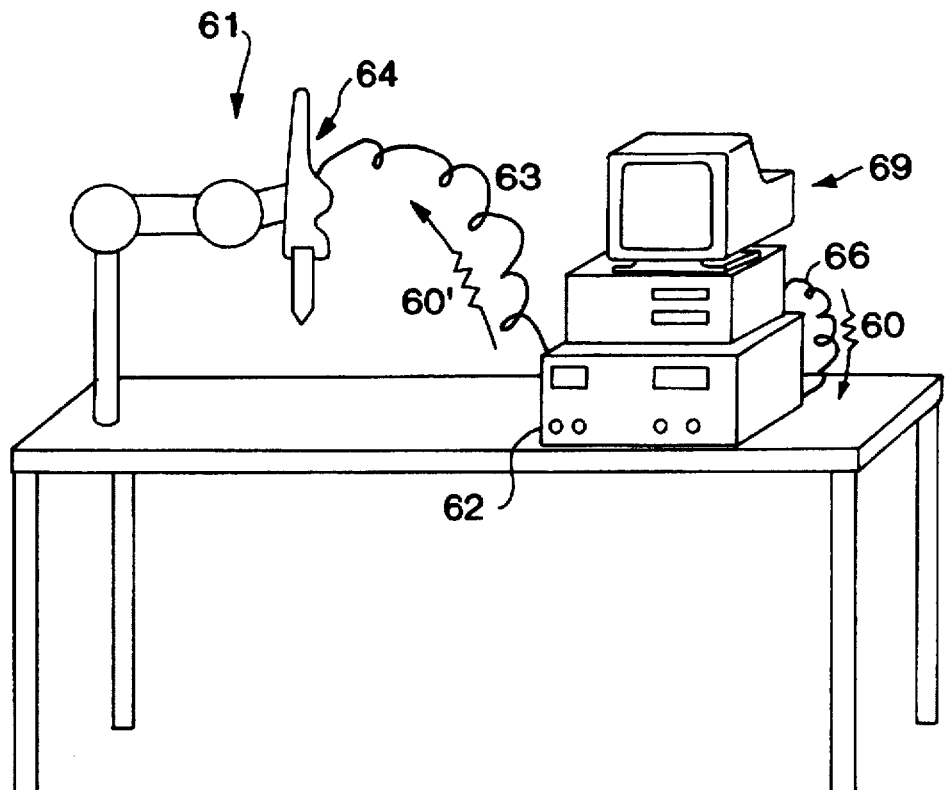
FIG. 6 shows the fluid dispenser system of the present invention integrated into an XYZ table, wherein the control unit receives input from a microprocessor.

Another embodiment of the present invention is shown in FIG. 6 wherein the fluid dispenser system of the present invention integrated into a robotic assembly device, such as XYZ table 61, wherein control unit 62 receives actuator signal 60 from microprocessor 69 via input tether 66 and, in turn, generates drive signal 60', which is sent to applicator 64 via output tether 68. In a related embodiment, applicator 64 may be mounted on a conventional XYZ table having a microprocessor capable of performing the functions of control unit 62, such that applicator 64 is controlled directly by the XYZ table microprocessor via output tether 68. In an even further embodiment, the fluid dispenser system of the present invention may be combined with a conventional XYZ table not having a microprocessor, such that control unit 62 is the sole means of controlling fluid dispensing.

Figure 7:
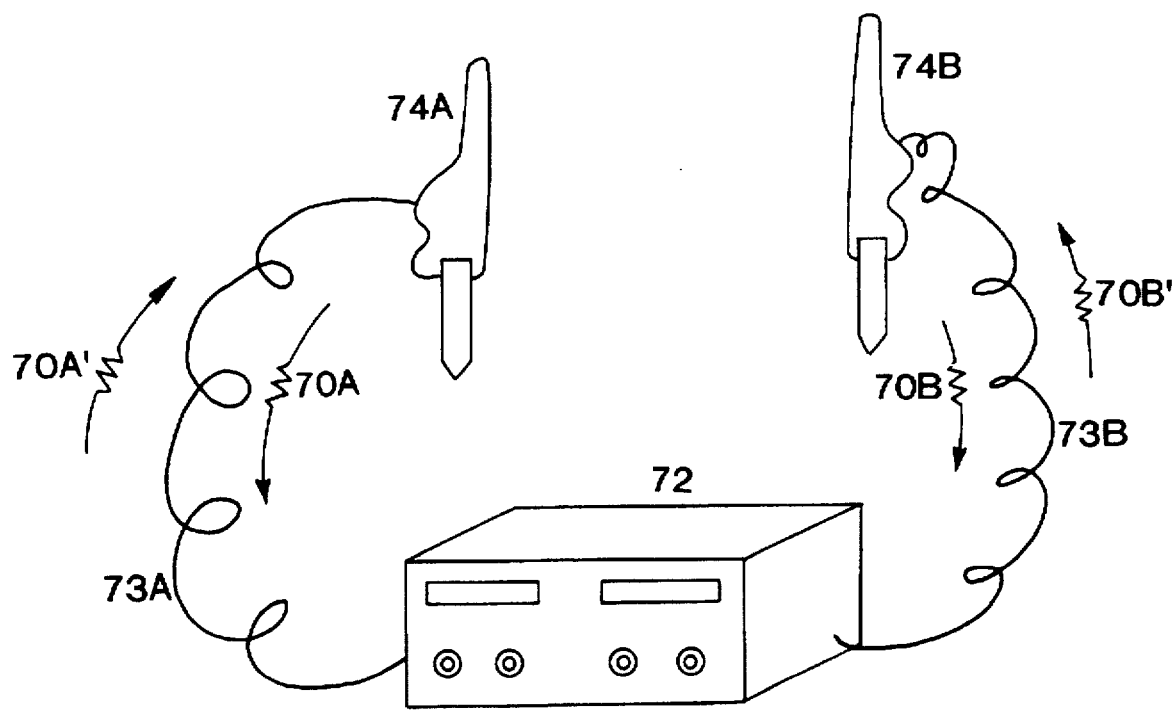
FIG. 7 shows an embodiment of the present invention wherein the control unit simultaneously controls two handheld applicators.

One further embodiment is shown in FIG. 7, wherein control unit 72 simultaneously controls two handheld applicators 74A and 74B via control tethers 73A and 73B. In this embodiment, control unit 72 is capable of (a) dual input of two separate actuator signals 70A and 70B from two separate applicators 74A and 74B, (b) dual signal processing in accordance with two separate pre-selected fluid volumes and two separate pre-selected flowrates, and (c) generation of two separate electronic drive signals 70A' and 70B' to the two separate applicators 74A and 74B. Thus, two operators simultaneously can each use separate applicators, or one operator can use two separate applicators either simultaneously or sequentially, as where bench-mixing of epoxy is desired.

It is understood that each of these embodiments allows for the use by the control unit of either a self-contained power source or a power cord that may draw power either from a storage device or from an AC-to-DC converter (to convert household current to current appropriate to drive the linear actuator).

The invention may be embodied in other specified forms without departing from the spirit or essential characteristics thereof. The present embodiments are therefore to be considered in all respects as illustrative and not restrictive, and all changes which come within the meaning and range or equivalency of the claims are therefore intended to be embraced therein.

What is claimed is:

1. An electronically controlled, positive-displacement fluid dispenser system comprising an electronic control unit capable of allowing the use of either preprogrammed settings or variable settings, a control tether, and an ergonomic, handheld applicator, wherein
a) the control unit has connected thereto an actuator signal generator,
b) the ergonomic, handheld applicator is in physical and electronic communication with the electronic control unit by the control tether,
c) the ergonomic, handheld applicator is capable of securly accommodating a conventional syringe and piston assembly, and
d) the ergonomic, handheld applicator is provided with a linear actuator that displaces a drive rod, to be disposed within said conventional syringe and piston assembly, a specific distance in response to an electronic drive signal generated by the control unit after the control unit receives an actuator signal generated by the actuator signal generator.

2. The electronically controlled, positive-displacement fluid dispenser system, as claimed in claim 1, wherein the electronic control unit has a power source selected from the group consisting of self-contained power sources, power cords that draw power from a storage device, and power cords that draw power from an AC-to-DC converter.

3. The electronically controlled, positive-displacement fluid dispenser system, as claimed in claim 1, wherein the syringe is securly accommodated by the handheld applicator by means of an adapter unit comprising a retaining ring and an adapter plate, wherein
a) the retaining ring has a body and a plurality of locking tabs disposed about the periphery thereof such that the locking tabs are disposed at a relatively normal angle from the retaining ring body,
b) the retaining ring body defines an axial void capable of accommodating a conventional medical syringe barrel
c) the adapter plate is a planar member that defines a corresponding plurality of peripheral voids capable of accommodating the plurality of retaining ring locking tabs such that rotation of the retaining ring relative to the adapter plate results in the locking tabs being locked into the peripheral voids, and
d) the adapter plate defines an axial void suitable for accommodating the drive rod. It is intended that adapter unit 12 be disposed within ergonomically designed cowling 18, although other constructions are possible, such as forming one face of retaining ring 14 into an ergonomically suitable shape.

4. The electronically controlled, positive-displacement fluid dispenser system, as claimed in claim 1, wherein the drive rod is provided therewith an engagable terminus, which matingly engages the piston.

5. The electronically controlled, positive-displacement fluid dispenser system as claimed in claim 1, wherein the actuator signal generator is a finger switch connected to the handheld applicator and the electronic drive signal is generated by the control unit after the control unit receives an actuator signal generated when the finger switch is depressed by the operator.

6. The electronically controlled, positive-displacement fluid dispenser system as claimed in claim 1, wherein the system is mounted to a stand and the actuator signal generator is a footpedal connected to the control unit and the electronic drive signal is generated by the control unit after the control unit receives an actuator signal generated when the footpedal is depressed by the operator.

7. The electronically controlled, positive-displacement fluid dispenser system as claimed in claim 1, wherein the actuator signal generator is a microprocessor and the electronic drive signal is generated by the control unit after the control unit receives an actuator signal from the microprocessor.

8. The electronically controlled, positive-displacement fluid dispenser system as claimed in claim 1, wherein the control unit is attached to two applicators, each having a linear actuator, and wherein the control unit is capable of dual input of two separate actuator signals from two separate actuator signal generators, dual signal processing in accordance with two separate pre-selected fluid volumes and two separate pre-selected flowrates, and generation of two separate electronic drive signals to the two separate linear actuators.

9. A method of extruding a precise volume of fluid from an electronically controlled, positive-displacement fluid dispenser system comprising an electronic control unit capable of allowing the use of either preprogrammed settings or variable settings, a control tether, and an ergonomic, handheld applicator, wherein a) the control unit has connected thereto an actuator signal generator,
   b) the ergonomic, handheld applicator is in physical and electronic communication with the electronic control unit by the control tether,
   c) the ergonomic, handheld applicator is capable of securly accommodating a conventional syringe and piston assembly, and
   d) the ergonomic, handheld applicator is provided with a linear actuator that displaces a drive rod, to be disposed within said conventional syringe and piston assembly, a specific distance in response to an electronic drive signal generated by the control unit after the control unit receives an actuator signal generated by the actuator signal generator, which method comprises the steps of:

i) selecting on the control unit the desired volume of fluid to be extruded;
   ii) positioning the ergonomic, handheld applicator so as to apply advantageously the fluid extruded;
   iii) generating an actuator signal to the control unit via the actuator signal generator, which generates in response an electronic drive signal from the control unit to the linear actuator that will drive the piston a specified distance in order to extrude the precise volume of fluid desired; wherein displacement of the drive rod engaged with the piston in the conventional syringe and piston assembly creates a positive pressure on the fluid contained in the syringe, thereby causing the extrusion of a precise volume of the fluid from the syringe.

10. The method of extruding a precise volume of fluid from an electronically controlled, positive-displacement fluid dispenser system, as claimed in claim 9, wherein wherein the electronic control unit has a power source selected from the group consisting of self-contained power sources, power cords that draw power from a storage device, and power cords that draw power from an AC-to-DC converter.

11. The electronically controlled, positive-displacement fluid dispenser system, as claimed in claim 9, wherein the syringe is securly accommodated by the handheld applicator by means of an adapter unit comprising a retaining ring and an adapter plate, wherein a) the retaining ring has a body and a plurality of locking tabs disposed about the periphery thereof such that the locking tabs are disposed at a relatively normal angle from the retaining ring body,
   b) the retaining ring body defines an axial void capable of accommodating a conventional medical syringe barrel
   c) the adapter plate is a planar member that defines a corresponding plurality of peripheral voids capable of accommodating the plurality of retaining ring locking tabs such that rotation of the retaining ring relative to the adapter plate results in the locking tabs being locked into the peripheral voids, and
   d) the adapter plate defines an axial void suitable for accommodating the drive rod. It is intended that adapter unit 12 be disposed within ergonomically designed cowling 18, although other constructions are possible, such as forming one face of retaining ring 14 into an ergonomically suitable shape.

12. The method of extruding a precise volume of fluid from an electronically controlled, positive-displacement fluid dispenser system, as claimed in claim 9, wherein the drive rod is provided therewith an engagable terminus, which matingly engages the piston in the conventional syringe and piston assembly.

13. The method of extruding a precise volume of fluid from an electronically controlled, positive-displacement fluid dispenser system, as claimed in claim 9, wherein the actuator signal generator is a finger switch connected to the handheld applicator and the electronic drive signal is generated by the control unit after the control unit receives an actuator signal generated when the finger switch is depressed by the operator.

14. The method of extruding a precise volume of fluid from an electronically controlled, positive-displacement fluid dispenser system, as claimed in claim 9, wherein the system is mounted to a stand and the actuator signal generator is a footpedal connected to the control unit and the electronic drive signal is generated by the control unit after the control unit receives an actuator signal generated when the footpedal is depressed by the operator.

15. The method of extruding a precise volume of fluid from an electronically controlled, positive-displacement fluid dispenser system, as claimed in claim 9, wherein the actuator signal generator is a microprocessor and the electronic drive signal is generated by the control unit after the control unit receives an actuator signal from the microprocessor.

16. The method of extruding a precise volume of fluid from an electronically controlled, positive-displacement fluid dispenser system, as claimed in claim 9, wherein the control unit is attached to two applicators each having a linear actuator and wherein the control unit is capable of dual input of two separate actuator signals from two separate actuator signal generators, dual signal processing in accordance with two separate pre-selected fluid volumes and two separate pre-selected flowrates, and generation of two separate electronic drive signals to the two separate linear actuators.

17. An electronically controllable, positive-displacement fluid dispenser comprising an applicator unit having a housing capable of accommodating a conventional syringe and piston assembly and provided with a linear actuator that displaces a drive rod, axially disposed therethrough and further having a terminal portion disposed within said conventional syringe and piston assembly, a specific distance in response to an electronic drive signal generated by an actuator.

18. The electronically controllable, positive-displacement fluid dispenser, as claimed in claim 17, wherein the actuator signal generator is an electric eye.

19. The electronically controllable, positive-displacement fluid dispenser, as claimed in claim 17, wherein the actuator signal generator is a footpedal.

20. The electronically controllable, positive-displacement fluid dispenser, as claimed in claim 17, wherein the actuator signal generator is a microprocessor.

21. The electronically controlled, positive-displacement fluid dispenser system, as claimed in claim 17, wherein the syringe is securly accommodated by the applicator unit by means of an adapter unit comprising a retaining ring and an adapter plate, wherein a) the retaining ring has a body and a plurality of locking tabs disposed about the periphery thereof such that the locking tabs are disposed at a relatively normal angle from the retaining ring body, b) the retaining ring body defines an axial void capable of accommodating a conventional medical syringe barrel c) the adapter plate is a planar member that defines a corresponding plurality of peripheral voids capable of accommodating the plurality of retaining ring locking tabs such that rotation of the retaining ring relative to the adapter plate results in the locking tabs being locked into the peripheral voids, and d) the adapter plate defines an axial void suitable for accommodating the drive rod.

22. An electronically controllable, positive-displacement fluid dispenser wherein the dispenser is mounted to a robotic assembly device having a microprocessor such that the dispenser is in signal communication therewith, and further wherein the dispenser comprises an applicator unit capable of securely accommodating a conventional syringe and piston assembly, and provided with a linear actuator that displaces a drive rod, axially disposed therethrough and further having a terminal portion disposed within said conventional syringe and piston assembly, a specific distance in response to an electronic drive signal generated by the microprocessor.

23. An electronically controllable, positive-displacement fluid dispenser wherein the dispenser is mounted to an XYZ table having a microprocessor such that the dispenser is in signal communication therewith, and further wherein the dispenser comprises an applicator unit capable of securely accommodating a conventional syringe and piston assembly, and provided with a linear actuator that displaces a drive rod, axially disposed therethrough and further having a terminal portion disposed within said conventional syringe and piston assembly, a specific distance in response to an electronic drive signal generated by the microprocessor.

* * * * *